US009433406B2

(12) United States Patent
Slagle et al.

(10) Patent No.: US 9,433,406 B2
(45) Date of Patent: Sep. 6, 2016

(54) CLAMP RING

(71) Applicant: Biomet Manufacturing, LLC, Warsaw, IN (US)

(72) Inventors: Paul Slagle, Leesburg, IN (US); Kevin Stone, Winona Lake, IN (US); Jacy Hoeppner, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 14/732,135

(22) Filed: Jun. 5, 2015

(65) Prior Publication Data

US 2015/0354751 A1    Dec. 10, 2015

Related U.S. Application Data

(60) Provisional application No. 62/008,694, filed on Jun. 6, 2014.

(51) Int. Cl.
| *A61B 1/32* | (2006.01) |
| *A61B 17/02* | (2006.01) |
| *F16M 13/02* | (2006.01) |
| *A61B 17/00* | (2006.01) |

(52) U.S. Cl.
CPC ........... *A61B 17/0293* (2013.01); *A61B 90/50* (2016.02); *A61B 90/57* (2016.02); *F16M 13/02* (2013.01); *A61B 17/0206* (2013.01); *A61B 2017/00477* (2013.01)

(58) Field of Classification Search
CPC ................. F16M 13/02; A61B 19/26; A61B 2019/267; A61B 17/0293; A61B 17/02
USPC ............... 248/316.1; 600/230, 228, 231, 234
See application file for complete search history.

(56) References Cited

U.S. PATENT DOCUMENTS

| 4,010,741 | A | * | 3/1977 | Gauthier | ............ | A61B 17/0293 600/233 |
| 4,457,300 | A | * | 7/1984 | Budde | ................ | A61B 17/0293 600/228 |
| 4,813,401 | A | * | 3/1989 | Grieshaber | ............ | A61B 17/02 600/226 |
| 5,967,973 | A | * | 10/1999 | Sherts | ................ | A61B 17/0293 600/205 |
| 6,030,340 | A | * | 2/2000 | Maffei | ............... | A61B 17/0206 600/228 |
| 6,190,312 | B1 | * | 2/2001 | Fowler, Jr. | ......... | A61B 17/0293 600/231 |
| 7,137,949 | B2 | * | 11/2006 | Scirica | ............... | A61B 17/0293 600/210 |
| 7,232,411 | B2 | * | 6/2007 | Dinkler, II | ............. | A61B 17/02 600/230 |
| 8,852,090 | B2 | * | 10/2014 | Friedrich | ............... | A61B 17/02 600/228 |

* cited by examiner

*Primary Examiner* — Anita M King
(74) *Attorney, Agent, or Firm* — Schwegman Lundberg & Woessner, P.A.

(57) ABSTRACT

A clamp ring includes a generally arced portion. The generally arced portion has a top half and a bottom half each having a guide channel formed therein, the top half and the bottom half each have an exterior portion and an interior portion defining boundaries of the guide channels. The interior portions together have a partially circular cross section with a number of interior reliefs formed therein and the exterior portions together have a partially circular cross section with a number of exterior reliefs formed therein that is greater than zero and equal to or greater than the number of interior reliefs formed in the interior portions.

18 Claims, 4 Drawing Sheets

CLAMP RING

CROSS REFERENCE TO RELATED APPLICATIONS

This is a non-provisional application based upon U.S. provisional patent application Ser. No. 62/008,694, entitled "RING SHAPE", filed Jun. 6, 2014, which is incorporated herein by reference.

BACKGROUND OF THE INVENTION

1. Field of the Invention

The present invention relates to surgical devices, and, more particularly, to clamp rings.

2. Description of the Related Art

During a surgical procedure, clamps are often used to hold various tools throughout the procedure. Typically, the clamps are connected to clamp holders to give the clamps a set position during the surgery. These clamps holders can be formed as straight sections connected together to form different shapes, such as octagons, that the clamps are screwed or bolted to. Such clamp holders can require the surgeon to use tools to lock the clamps to the holders, which can be inconvenient to sterilize for use in a surgical environment. Further, such clamp holders can make it difficult to adjust where the clamps are held during the surgical procedure.

What is needed in the art is a clamp holder that can overcome some of the previously mentioned disadvantages.

SUMMARY OF THE INVENTION

The present invention provides a clamp ring with a shape that allows a clamp body to continuously slide along a generally arced portion of the clamp ring.

The invention in one form is directed to a clamp ring including a generally arced portion. The generally arced portion has a top half and a bottom half each having a guide channel formed therein, the top half and the bottom half each have an exterior portion and an interior portion defining boundaries of the guide channels. The interior portions together have a partially circular cross section with a number of interior reliefs formed therein and the exterior portions together have a partially circular cross section with a number of exterior reliefs formed therein that is greater than zero and equal to or greater than the number of interior reliefs formed in the interior portions.

The invention in another form is directed to a clamp ring including: a generally arced portion having a top half and a bottom half, the top half and said bottom half each having a curved track formed thereon; and at least one straight portion continuous with the generally arced portion, the at least one straight portion having a top half and a bottom half each having a straight track formed thereon continuous with the curved tracks. The continuous straight tracks and curved tracks form ring tracks each defining a track length. The ring tracks allow a clamp to continuously slide along the track lengths.

The invention in yet another form is directed to a clamp ring including a generally arced portion. The generally arced portion has a top half and a bottom half each having at least one guide channel formed therein, the top half and the bottom half each have an exterior portion and an interior portion each defining a boundary of a guide channel. The interior portions together have a partially circular cross section with a number of interior reliefs formed therein and the exterior portions together have a partially circular cross section with a number of exterior reliefs formed therein that is greater than zero and equal to or greater than the number of interior reliefs formed in the interior portions.

An advantage of the present invention is a clamp can be slid continuously along a length of the generally arced portion to adjust its relative position.

Another advantage is clamps can be placed and slide on both the interior and exterior portions of the clamp simultaneously.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one embodiment of the invention and such exemplification is not to be construed as limiting the scope of the invention in any manner.

DETAILED DESCRIPTION OF THE INVENTION

Figure 1:
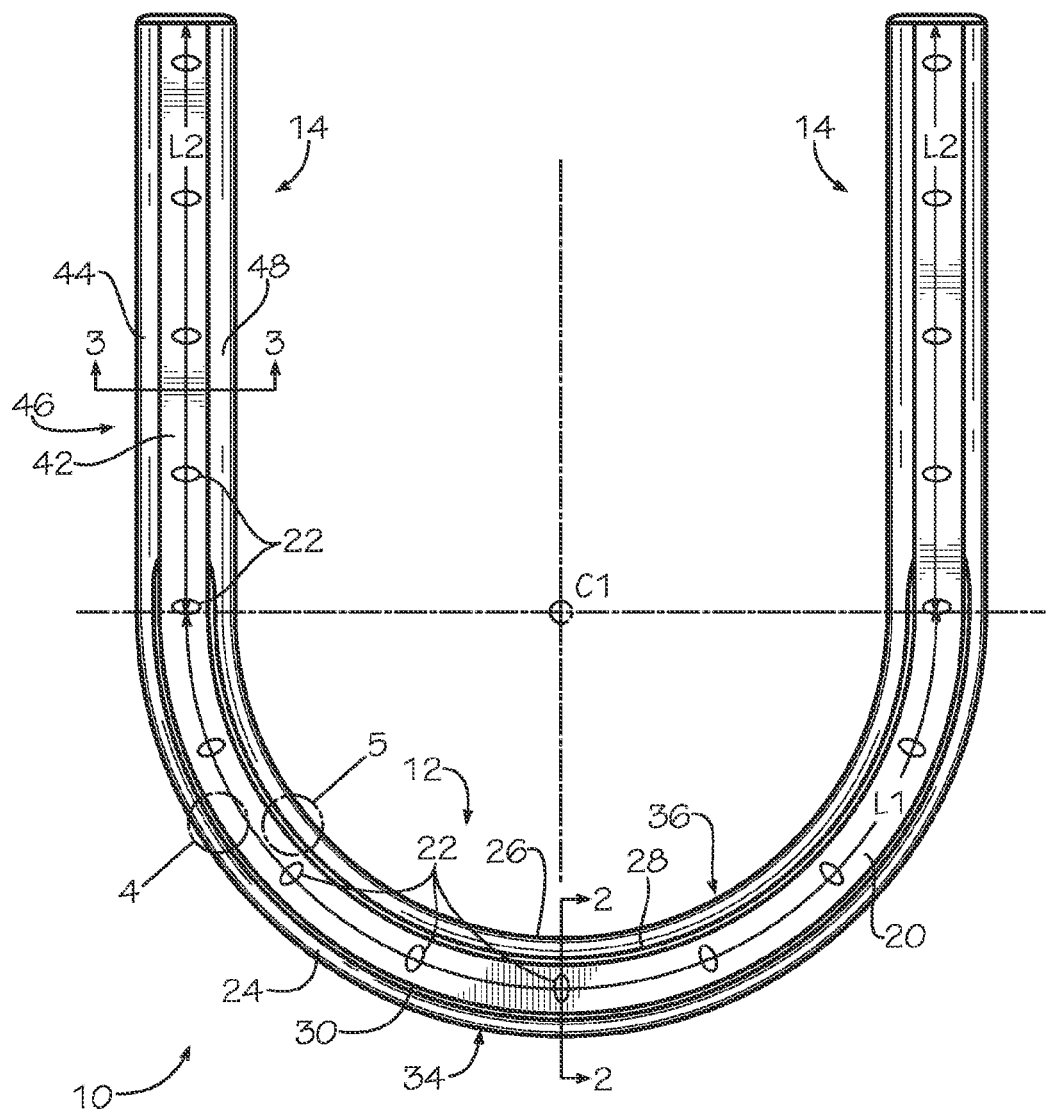
FIG. 1 is a top view of an embodiment of a clamp ring formed according to the present invention.

Referring now to the drawings, and more particularly to FIG. 1, there is shown an embodiment of a clamp ring 10 according to the present invention which generally includes a generally arced portion 12. The clamp ring 10 can also include one or more straight portions 14 that are continuous with the generally arced portion 12 by being formed integrally with the generally arced portion 12, connection to the generally arced portion 12, or otherwise held adjacent to the generally arced portion 12 to form an effectively continuous clamp ring 10. The generally arced portion 12, as shown, can be formed to have a semi-circle shape extending 180 degrees about an arc center C1, although other arc lengths are also contemplated. As used herein, "generally arced" signifies that the generally arced portion 12 can deviate from a perfectly arced shape due to standard manufacturing tolerances. The clamp ring 10 can be formed of any type of material in any desired way.

Figure 2:
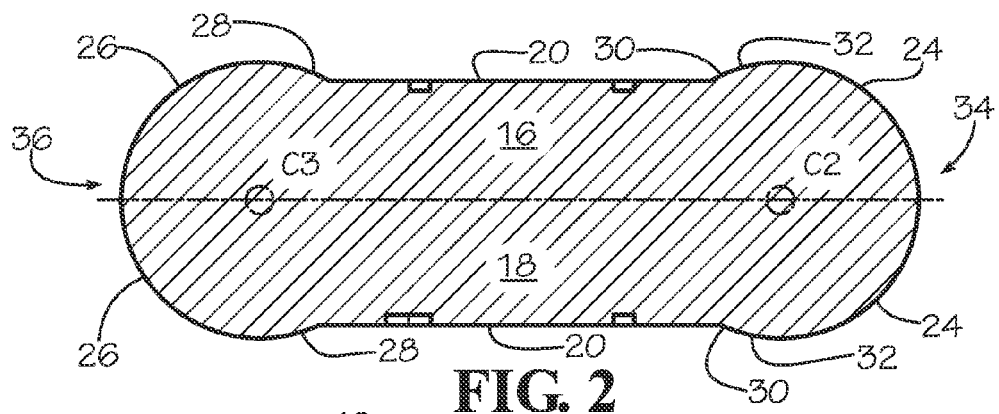
FIG. 2 is a cross-sectional view of a generally arced portion of the clamp ring shown in FIG. 1 taken along line 2-2.

Referring now to FIG. 2, a cross-section through the generally arced portion 12 is shown. The generally arced portion 12 includes a top half 16 and a bottom half 18 forming the generally arced portion 12. It should be appreciated that the top half 16 and bottom half 18 described herein are arbitrary divisions of the generally arced portion 12 to better describe the geometry of the generally arced portion 12 and that the top half 16 and bottom half 18 can either be integrally formed together or separable from one another. A guide channel 20 is formed into both the top half 16 and bottom half 18, i.e., on both sides of the generally arced portion 12, that can stabilize the sliding movement of a clamp along the clamp ring 10. The guide channels 20 can be formed into the top half 16 and bottom half 18 so that the guide channel 20 is defined by at least one flat surface. It should be appreciated that while only one guide channel 20 is shown as being formed in the top half 16 and bottom half 18, it is contemplated that one or both of the top half 16 and bottom half 18 could have two or more guide channels formed therein that are spaced apart from each other. As can be seen in FIG. 1, one or more visual indicators 22, shown as raised portions of material, can be formed in the guide channels 20 so that a user can measure where different clamps are held relative to each other on the clamp ring 10 or the relative position of one or more clamps on the clamp ring 10.

The top half 16 and bottom half 18 each have an exterior portion 24 and an interior portion 26. The exterior portions 24 of the top half 16 and bottom half 18 together have a partially circular cross-section which can be defined about exterior center C2, and the interior portions 26 of the top half 16 and bottom half 18 together have a partially circular cross-section which can be defined about interior center C3. The exterior center C2 and interior center C3 can be aligned with one another, as shown in FIG. 2, and define boundaries of the top half 16 and bottom half 18. The exterior portions 24 and the interior portions 26 each define a boundary on one side of the guide channels 20 such that when one guide channel 20 is formed in the top half 16 and bottom half 18, the guide channel 20 formed in both halves 16, 18 is defined between the exterior portions 24 and interior portions 26.

The interior portions 26 can have a number of reliefs 28 formed therein that disrupt the circular cross-section shape of the interior portions 26. As shown in FIG. 2, one interior relief 28 can be formed in each interior portion 26 that is formed continuously with the guide channels 20. In other words, the reliefs 28 can be formed in the interior portions 26 between the flat surface of the guide channels 20 and the circular cross-sectional shape of the interior portions 26. While one relief 28 is shown being formed in the interior portions 26, the number of reliefs could be zero or more than one relief 28 can be formed in the interior portions 26. The reliefs 28 can be formed into the interior portions 26 by cutting a straight edge into the material of the circular cross-section, providing a grasping ledge on the interior portions 26. The significance of the reliefs 28 formed in the interior portions 26 will be discussed further herein.

The exterior portions 24 have at least one relief 30, 32 formed therein that disrupt the circular cross-section shape of the exterior portions 24. As shown in FIG. 2, the exterior portions 24 can have a number of reliefs, shown as two exterior reliefs 30 and 32, formed therein that is equal to or greater than the number of reliefs 28 formed in the interior portions 26. Like the interior reliefs 28, the exterior reliefs 30 and 32 disrupt the circular cross-section shape of the exterior portions 24 and can provide a grasping ledge on the exterior portions 24. Unlike the interior portion 26, the exterior portion 24 must have at least one exterior relief 30 or 32 formed therein to provide a smooth sliding of a clamp across the generally arced portion 12. This arises from the curving nature of the exterior portions 24 of the generally arced portion 12, which together can be referred to as an exterior side 34 of the generally arced portion 12, that does not occur in the interior portions 26, which together can be referred to as an interior side 36 of the generally arced portion 12. Without having any reliefs 30 or 32 formed in the exterior side 34 of the generally arced portion 12, clamps sliding along the exterior side 34 can get caught or slip off the exterior side 34, resulting in an unstable clamping. The reliefs 30 and 32 can therefore allow for a clamp to stably grasp the exterior side 34 of the generally arced portion 12.

Figure 3:
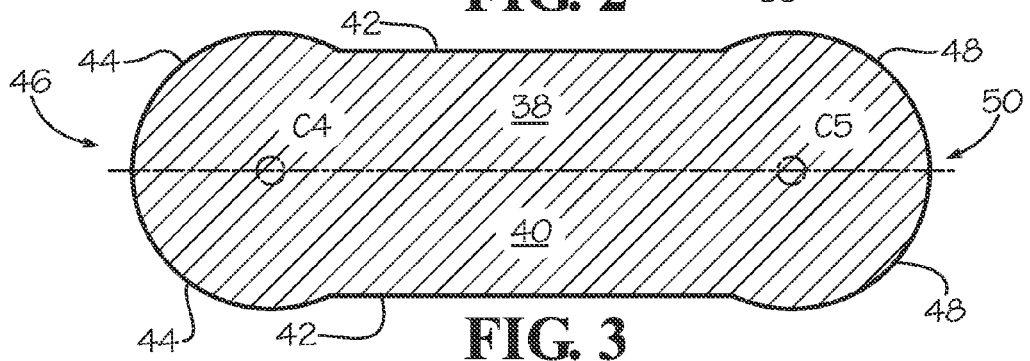
FIG. 3 is a cross-sectional view of a straight portion of the clamp ring shown in FIG. 1 taken along line 3-3.

Referring now to FIG. 3, a cross-section through one of the straight portions 14 is shown. The straight portions 14, as shown, are formed similarly to the generally arced portion 12 and have a top half 38, a bottom half 40, and a guide channel 42 formed between the top half 38 and bottom half 40, which define boundaries for the guide channel 42. The guide channel 42 formed in the straight portions 14 can be continuous with the guide channel 20 formed in the generally arced portion 12. The top half 38 and bottom half 40 can each have an exterior portion 44, the exterior portions 44 collectively forming an exterior side 46, as well as an interior portion 48, the interior portions 48 collectively forming an interior side 50. Unlike the exterior portions 24 and interior portions 26 of the generally arced portion 12, the exterior portions 44 and interior portions 48 of the straight portions 14 do not need to have any reliefs formed therein, due to there being no curvature in the sliding path along the portions 44 and 48. The exterior portions 44 and interior portions 48 of the straight portions 14 can therefore have partially circular cross-sections defined about exterior center C4 and interior center C5, respectively, that are uninterrupted by reliefs formed therein. Put another way, the exterior portions 44 and interior portions 48 of the straight portions 14 can have generally circular shapes all the way up to the guide channels 42, of which the exterior portions 44 and interior portions 48 serve as boundaries.

Figure 4:
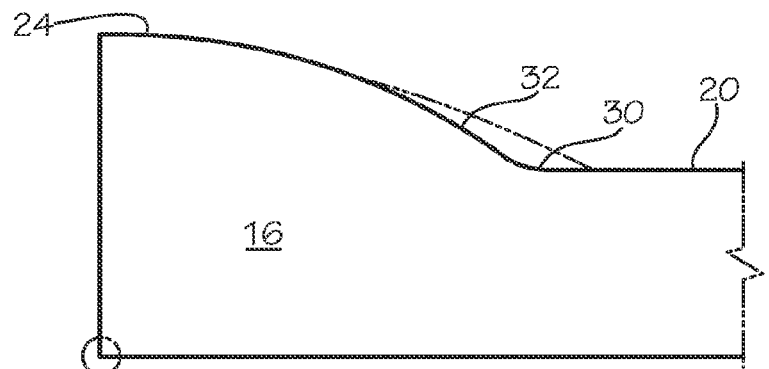
FIG. 4 is a partial cut-away view of an exterior side of the clamp ring shown in FIG. 1.

Referring now to FIG. 4, a portion of the exterior portion 24 of the top half 16 of the generally arced portion 12 is shown in better detail to illustrate the difference in shape between this exterior portion 24 of the generally arced portion 12 and one or both of the exterior portions 44 of the straight portions 14. As can be seen, the first exterior relief 30 formed in the exterior portion 24 that is continuous with the guide channel 20 can extend into the second exterior relief 32 formed in the exterior portion 24. In other words, the second exterior relief 32 can be formed in the exterior portion 24 so that it is spaced apart from the guide channel 20. For comparison to an exterior portion 44 of the straight portion 14, a corresponding material difference between the exterior portion 44 of the straight portion 14 and the exterior portion 24 of the generally arced portion 12 is drawn in as dashed lines. In other words, the dashed lines represent the material that can be removed from an exterior portion 44 of the straight portion 14 to form the reliefs 30 and 32 in the exterior portion 24 of the generally arced portion 12.

Figure 5:
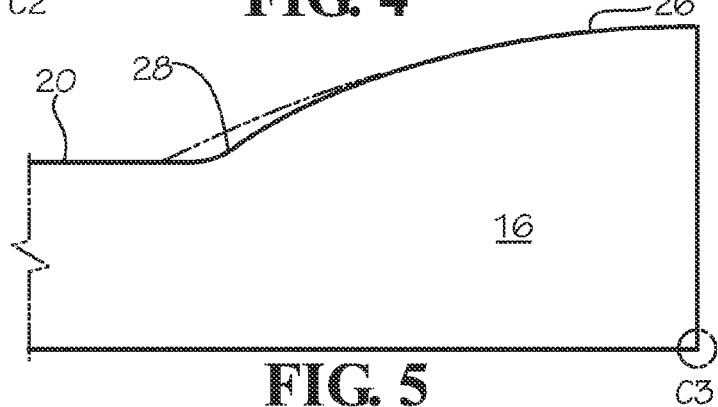
FIG. 5 is a partial cut-away view of an interior side of the clamp ring shown in FIG. 1.

Referring now to FIG. 5, a portion of the interior portion 26 of the top half 16 of the generally arced portion 12 is shown in better detail to illustrate the difference in shape between this interior portion 26 of the generally arced portion 12 and one or both of the interior portions 46 of the straight portions 14. As can be seen, the interior relief 28 formed in the interior portion 26 is continuous with the guide channel 20. For comparison to an interior portion 46 of the straight portion 14, a corresponding material difference between the interior portion 46 of the straight portion 14 and the interior portion 26 of the generally arced portion 12 is drawn in as dashed lines. In other words, the dashed lines represent the material that can be removed from an interior portion 46 of the straight portion 14 to form the relief 28 in the interior portion 26 of the generally arced portion 12. As can be seen by comparing FIGS. 4 and 5 and assuming the exterior portion 24 and interior portion 26 are both formed by cutting one or more reliefs into the same shape, the material difference between the exterior portion 24 and the interior portion 26 is different due to the differing number of reliefs formed in the exterior portion 24 and the interior portion 26. The exterior portion 24 material difference, illustrated in FIG. 4, can be larger than the interior portion 26 material difference, illustrated in FIG. 5. This difference is due in part to the exterior portion 24 having a greater number of reliefs 30 and 32 than the interior portion 26, and also because the exterior reliefs 30 and 32 can be continuous leading to the second exterior relief 32 being deeper than the interior relief 28. In other words, the interior relief 28 can be shallower than the second exterior relief 32.

Figure 6:
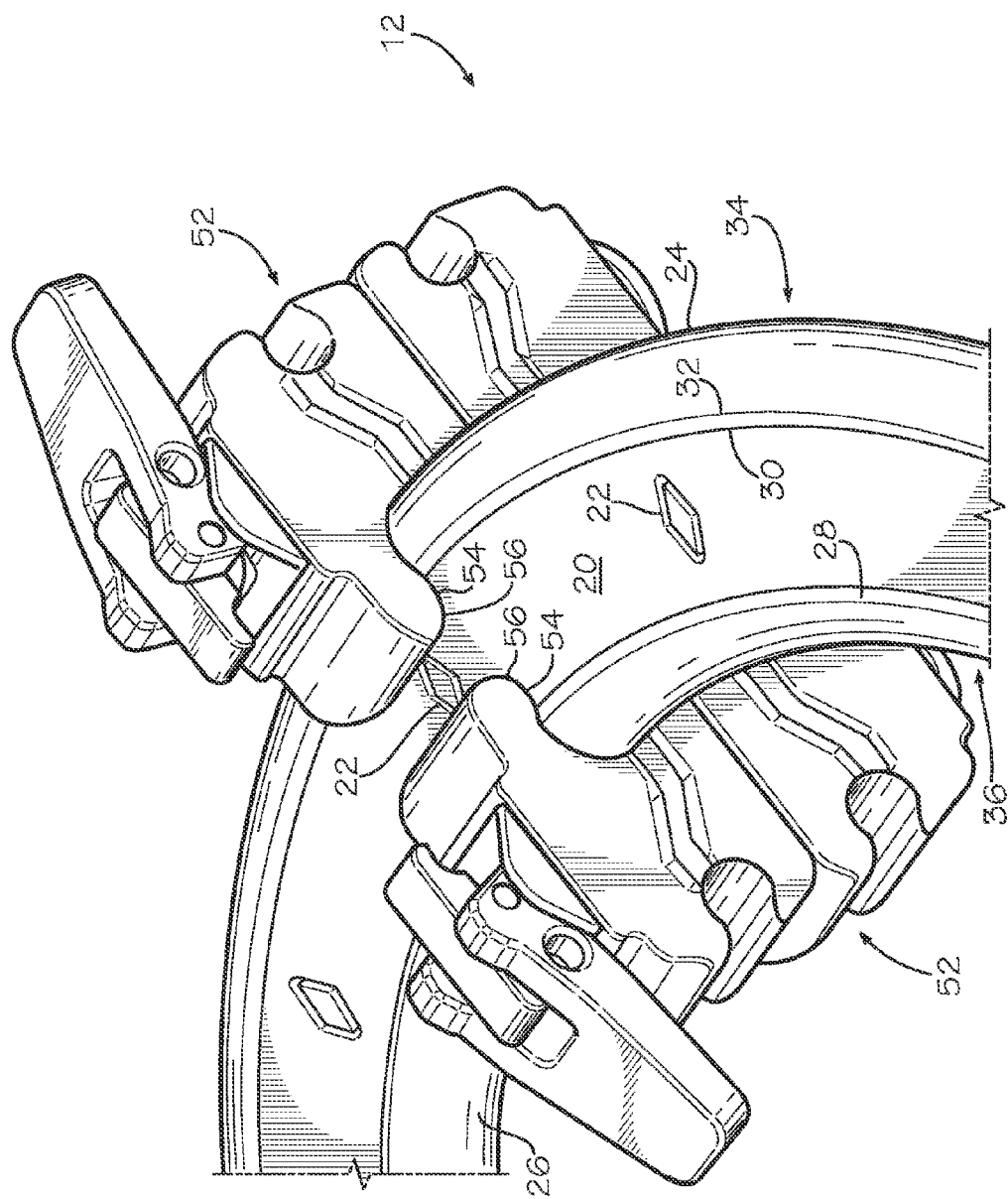
FIG. 6 is a perspective view of two clamps slidably connected to the clamp ring shown in FIG. 1.

Referring now to FIG. 6, two identical clamps 52 are shown in a sliding position along the generally arced portion 12 of the clamp ring 10. As can be seen, one of the clamps 52 is sliding along the interior side 36 of the generally arced portion 12 and the other clamp 52 is sliding along the exterior side 34 of the generally arced portion 12 so that the two clamps 52 are aligned on the generally arced portion 12, but on opposite sides. Flats 54 of the clamps 52 rest on the guide channel 20 to help stabilize the clamps 52. The clamps 52 also have first clamp reliefs 56 formed near the flats 54 that allow the clamps 52 to grip the interior relief 28 of the interior portions 26.

Figure 7:
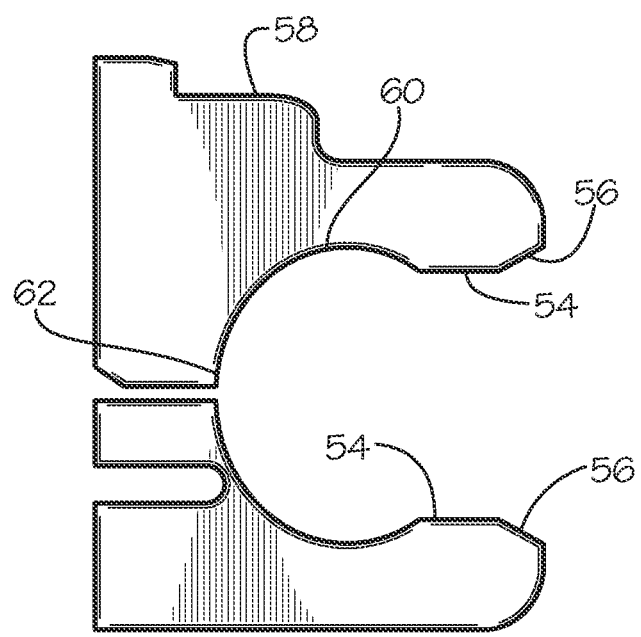
FIG. 7 is a side view of one of the clamp bodies shown in FIG. 6.
Figure 8:
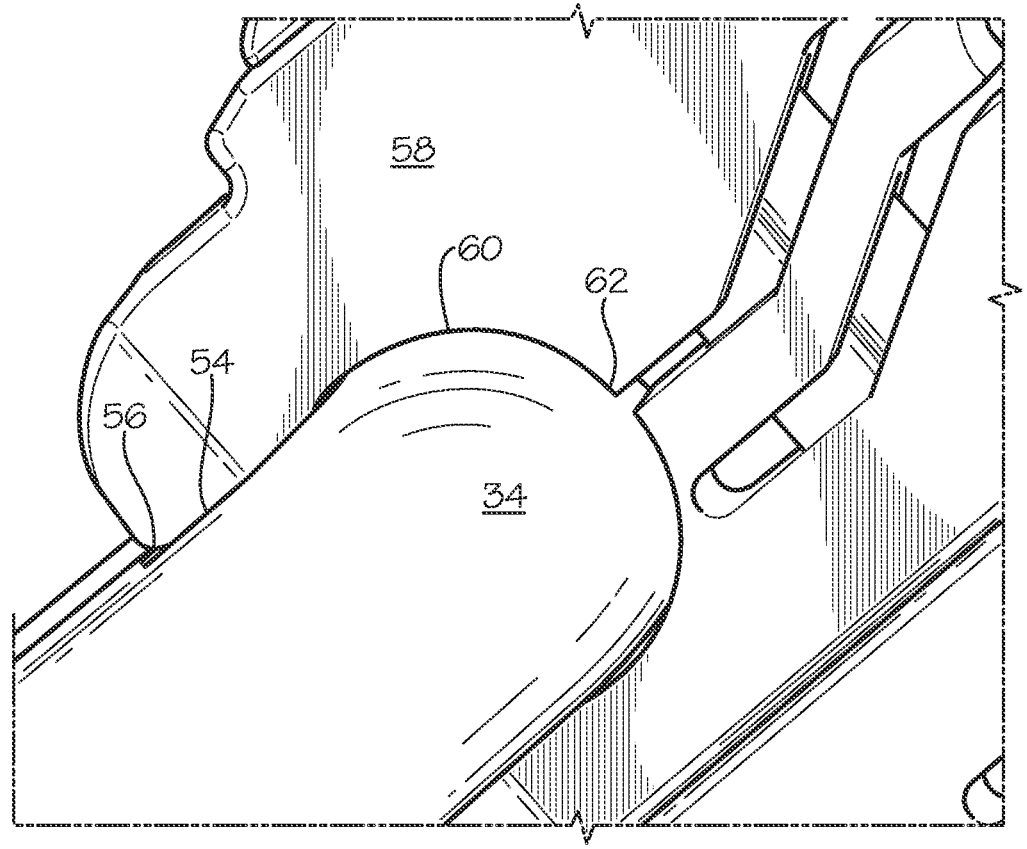
FIG. 8 is a perspective view of one of the clamps shown in FIG. 6 slidably connected to the clamp ring.

Referring now to FIG. 7, a side view of a clamp body 58 of the clamps 52 is shown. As can be seen, the clamp body 58 can have a clamping recess 60 formed therein that is circular in shape to match the shape of the exterior portions 24 and 44 and the interior portions 26 and 48 of the clamp ring 10. The clamp body 58 can also have a second clamp relief 62 formed near a back of the clamping recess 60 that allows the clamp 52 to better grip the exterior side 34 of the generally arced portion 12 due to the reliefs 30 and 32 formed in the exterior portions 24. As shown in FIG. 8, a part of the exterior side 34 is grasped within the second clamp relief 62 as the clamp 52 slides along the exterior side 34 to better stabilize the clamp 52 on the exterior side 34 of the generally arced portion 12. When the clamps 52 are grasping the straight portion 14, the flats 54 pressed against the guide channel 42 can provide sufficient grip on the exterior side 46 and interior side 50. This allows the clamps 52 to slide along a curved length L1 of the generally arced portion 12, which can be equal to the arc length defined about the arc center C1, and continuously slide from the generally arced portion 12 to the straight portions 14 and along straight lengths L2 of the straight portions 14. The clamps 52 can therefore continuously slide along the entire length of the clamp ring 10, which can be the sum of the curved length L1 and the one or more straight lengths L2, smoothly and without the need to adjust the clamps 52 as they slide.

It should therefore be appreciated that the top half 16 and bottom half 18 of the generally arced portion 12 have a curved track formed thereon, defined by geometry of the exterior side 34 and the interior side 36, that can be continuous with a straight track that is formed in the top half 38 and bottom half 40 of the one or more straight portions 14 and is defined by geometry of the exterior side 46 and the interior side 50. The curved track can define the previously described curved length L1 and the straight track(s) can define the previously described straight lengths L2. Since the curved track and the straight track(s) can be continuous, together they can define ring tracks formed in the clamp ring 10 defining a track length, which is equal to the combined length of the curved length L1 and the one or more straight lengths L2. Clamps 52 can therefore slide continuously along the entirety of the track length L1, L2 on both the exterior sides 34 and 46 and the interior sides 36 and 50 simultaneously.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A clamp ring, comprising:
a generally arced portion arced within a plane,
said generally arced portion having a top half and a bottom half disposed on opposite sides of the plane,
the top half and bottom half each having a guide channel formed therein,
said top half and said bottom half each having an exterior portion and an interior portion defining boundaries of said guide channels,
said interior portions together having a partially circular cross section with a number of interior reliefs formed therein and said exterior portions together having a partially circular cross section with a number of exterior reliefs formed therein that is greater than zero and one of equal to and greater than said number of interior reliefs formed in said interior portions.

2. The clamp ring according to claim 1, wherein said interior portions have at least one interior relief formed continuously with said guide channel.

3. The clamp ring according to claim 2, wherein said exterior portions have at least one exterior relief formed continuously with said guide channel.

4. The clamp ring according to claim 3, wherein said exterior portions have at least one exterior relief spaced apart from said guide channel.

5. The clamp ring according to claim 1, wherein said top half and said bottom half each include at least one visual indicator formed in said guide channel.

6. The clamp ring according to claim 1, further comprising at least one straight portion continuous with said generally arced portion, said at least one straight portion having a top half and a bottom half each having a guide channel formed therein, said top half and said bottom half each having an exterior portion and an interior portion defining boundaries of said guide channel, said interior portions together having a partially circular cross section and said exterior portions together having a partially circular cross section.

7. The clamp ring according to claim 6, wherein said at least one straight portion has no reliefs formed therein.

8. The clamp ring according to claim 6, wherein said exterior portions and said interior portions each allow continuous sliding of a clamp body along an entire length of said generally arced portion and said at least one straight portion.

9. The clamp ring according to claim 1, wherein said number of interior reliefs is greater than zero.

10. The clamp ring according to claim 1, wherein said exterior portions and said interior portions each allow continuous sliding of a clamp body along an entire length of said generally arced portion.

11. The clamp ring according to claim 1, wherein said exterior portions have at least two exterior reliefs formed therein.

12. The clamp ring according to claim 1, wherein said interior portions have at least one interior relief formed therein, said at least one interior relief being shallower than at least one of said exterior reliefs.

13. A clamp ring, comprising:
a generally arced portion arced within a plane, said generally arced portion having a top half and a bottom half disposed on opposite sides of the plane, said top half and said bottom half each having a curved track formed thereon; and
at least one straight portion continuous with said generally arced portion, said at least one straight portion having a top half and a bottom half each having a straight track formed thereon continuous with said curved tracks, wherein continuous straight tracks and curved tracks form ring tracks each defining a track length, said ring tracks allowing a clamp to continuously slide along said track lengths.

14. The clamp ring according to claim 13, wherein said generally arced portion and said at least one straight portion each have an exterior side and an interior side defining boundaries of said ring tracks, at least one of said generally arced portion and said at least one straight portion allowing a clamp to slide along said exterior side simultaneously with a clamp sliding along said interior side.

15. A clamp ring, comprising:
a generally arced portion arced within a plane, said generally arced portion having a top half and a bottom half disposed on opposite sides of the plane,
the top half and bottom half each having at least one guide channel formed therein,
said top half and said bottom half each having an exterior portion and an interior portion each defining a boundary of at least one guide channel,
said interior portions together having a partially circular cross section with a number of interior reliefs formed therein and said exterior portions together having a partially circular cross section with a number of exterior reliefs formed therein that is greater than zero and one of equal to and greater than said number of interior reliefs formed in said interior portions.

16. The clamp ring according to claim 15, further comprising at least one straight portion continuous with said generally arced portion, said at least one straight portion having a top half and a bottom half each having at least one guide channel formed therein, said top half and said bottom half each having an exterior portion and an interior portion each defining a boundary of at least one guide channel, said interior portions together having a partially circular cross section and said exterior portions together having a partially circular cross section.

17. The clamp ring according to claim 16, wherein said at least one straight portion has no reliefs formed therein.

18. The clamp ring according to claim 16, wherein said exterior portions and said interior portions each allow continuous sliding of a clamp body along an entire length of said generally arced portion and said at least one straight portion.

* * * * *